(12) United States Patent
Licari et al.

(10) Patent No.: US 6,562,602 B2
(45) Date of Patent: May 13, 2003

(54) FERMENTATION AND PURIFICATION OF MYCOLACTONES (75) Inventors: Peter Licari, Fremont, CA (US); Robert Arslanian, Pacifica, CA (US); Lawrence Cadapan, San Francisco, CA (US); John Carney, San Bruno, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 0 days.

(21) Appl. No.: 09/921,666

(22) Filed: Aug. 3, 2001

(65) Prior Publication Data

US 2002/0086375 A1 Jul. 4, 2002

Related U.S. Application Data

(60) Provisional application No. 60/222,649, filed on Aug. 3, 2000.

(51) Int. Cl.[7] .................................................. C12P 17/02
(52) U.S. Cl. .................................................. 435/123
(58) Field of Search .................................................. 435/123

(56) References Cited

PUBLICATIONS

Cadapan, L. et al. (2001) *FEMS Microbiology Letters* 205(2):385–389.

George, K. et al. (1998) *Infection and Immunity* 66(2):587–593.

George, K. et al. (1999) *Science* 283(5403):854–857.

Report of the 3rd WHO Advisory Group Meeting on Buruli Ulcer (Mar., 2000), On Line!, XP002201041. Retrieved from the Internet: <URL:http:/www.who.int/gtb–buruli/activities/PDF/2000_meeting_report_(BU).pdf> retrieved on Jun. 3, 2002! pp. 59–60.

Report of the 4th WHO Advisory Group Meeting on Buruli Ulcer (Mar., 2001), On Line!, XP002201042. Retrieved from the Internet: >URL:http:/www.who.int/gtb–buruli/activities/PDF/2001_Final_Report.pdf> retrieved on Jun. 3, 2002! pp. 57–59.

George et al., Science (1999) 283:854–857.

Gunawardana et al., JACS (1999) 121:6092–6093.

Mve–Obiang et al., FEMS Microbiol. Lett. (1999) 181:153–157.

Nyabenda et al., J. Biol. Standard (1988) 16:259–267.

Palomino et al., J. Clin. Microbiol. (1998) 36(11):3420–3422.

Palomino and Portaels, J. Clin. Microbiol. (1998) 36(2):402–408.

Pimsler et al., J. Infect. Dis. (1988) 157(3):577–580.

Read et al., Infection & Immun. (1974) 9(6):1114–1122.

*Primary Examiner*—Herbert J. Lilling
(74) *Attorney, Agent, or Firm*—Morrison & Foerster LLP; Jose Aparicio; Kevin Kaster

(57) ABSTRACT

Fermentation based methods for producing mycolactones allows one to produce large quantities of mycolactones, which can be purified by extraction and chromatography to yield pure preparations of mycolactones A, B, C, and D.

6 Claims, 5 Drawing Sheets

FERMENTATION AND PURIFICATION OF MYCOLACTONES

This application asserts priority to U.S. Provisional Application No. 60/222,649 filed Aug. 3, 2000 by inventors Peter Licari, Robert Arslanian, Lawrence Cadapan and John Carney entitled FERMENTATION AND PURIFICATION OF MYCOLACTONES which is incorporated herein by reference.

FIELD OF THE INVENTION

The present invention provides methods for preparing mycolactones by fermentation and novel mycolactone compounds useful in the treatment of disease conditions. The invention relates to the fields of chemistry, molecular biology, animal and human health sciences, and medicine.

BACKGROUND OF THE INVENTION

*Mycobacterium ulcerans* causes a severe skin disease, Buruli ulcer, which is characterized by extensive necrosis in the absence of an acute inflammatory response. The causative agent of the disease was first identified as a diffusible toxic agent (see Read et al., June 1974, Cytotoxic activity of *Mycobacterium ulcerans*, *Infection & Immun.* 9(6): 1114–1122, incorporated herein by reference). Further analysis identified that the agent is a polyketide (see George et al., Feb. 5, 1999, Mycolactone: A polyketide toxin from *Mycobacterium ulcerans* required for virulence, *Science* 283: 854–857, incorporated herein by reference). Recently, the complete structural determination of two structurally related agents, called mycolactones A and B, has been reported (see Gunawardana et al., 1999, Characterization of novel macrolide toxins, mycolactones A and B, from a human pathogen, *Mycobacterium ulcerans*, *JACS* 121: 6092–6093, incorporated herein by reference).

The cytotoxic nature of the mycolactones, as well as their ability to suppress the immune response, indicates that the compounds have therapeutic potential as anti-cancer agents and immunosuppressants (see the references cited supra and Pimsler et al., March 1988, Immunosuppressive properties of the soluble toxin from *Mycobacterium ulcerans*, *J. Infect. Dis.* 157(3): 577–580, incorporated herein by reference). However, despite extensive efforts to develop fermentation conditions suitable for large-scale growth of *Mycobacterium ulcerans* and related organisms such as *M. bovis* (see e.g. Mve-Obiang et al., 1999, Growth and cytotoxic activity by *Mycobacterium ulcerans* in protein-free media, *FEMS Microbiol. Lett.* 181: 153–157; Nyabenda et al., 1988, The production of mycobacterial antigens by homogeneous culture in a fermentor, *J. Biol. Standard.* 16: 259–267; Palomino & Portaels, February 1998, Effects of decontamination methods and culture conditions on viability of *Mycobacterium ulcerans* in the BACTEC system, *J. Clin. Microbiol.* 36(2): 402–408; and Palomino et al., November 1998, Effect of oxygen on growth of *Mycobacterium ulcerans* in the BACTEC system, *J. Clin. Microbiol* 36(11): 3420–3422, each of which is incorporated herein by reference), cultivation of the organism remains difficult, limiting the availability of the compounds for testing and clinical trials.

There remains a need for fermentation processes by which large scale cultures of *Mycobacterium ulcerans* can be obtained and from which useful quantities of mycolactones could be prepared. The present invention meets that need and provides as well, as one important benefit, novel naturally produced mycolactones in purified form that were heretofore undiscovered due to the lack of suitable fermentation processes.

SUMMARY OF THE INVENTION

In a first embodiment, the present invention provides methods for the production of mycolactones by fermentation. The methods are readily scalable and can be used to produce the mycolactones in amounts sufficient for clinical trials and commercialization. The methods enable the cultivation of *Mycobacterium ulcerans* in a dispersed suspension culture (e.g., fermentation or spinner flasks) and the production of the mycolactones at concentrations greater than that observed in T flasks.

In a second embodiment, the present invention provides improved media formulations that allow scale-up of cultures for the production of mycolactones and improve the production of mycolactone from *Mycobacterium ulcerans*.

In a third embodiment, the present invention also provides a robust and scalable method for the purification of mycolactones based on extraction and chromatography.

In a fourth embodiment the present invention provides novel mycolactone compounds isolatable from *Mycobacterium ulcerans* in purified form.

These and other embodiments, modes, and aspects of the invention are described in more detail in the following brief description of the figure, detailed description of the invention, the examples, and claims set forth below.

DETAILED DESCRIPTION OF THE INVENTION

In a first embodiment, the present invention provides methods for the production of mycolactones by fermentation. The methods are readily scalable and can be used to produce the mycolactones in amounts sufficient for clinical trials and commercialization. The methods enable the cultivation of *Mycobacterium ulcerans* in a dispersed suspension culture (e.g., fermentation or spinner flasks) and the production of the mycolactones at concentrations greater than that observed in T flasks.

Prior to the present invention, *Mycobacterium ulcerans* was grown in stationary T-flasks to produce mycolactone; attempts to cultivate the organism in suspension culture were unsuccessful. Using the methods of the present invention, one can grow the cells in a dispersed suspension culture (e.g. fermentation or spinner flasks) and produce mycolactone in concentrations greater than that observed in T flasks. This allows for scale-up of cultures for the production of mycolactones in commercially relevant quantities.

In a second embodiment, the present invention provides improved media formulations that allow scale-up of cultures for the production of mycolactones and improve the production of mycolactone from *Mycobacterium ulcerans*. The improved media formulations increase the amount of mycolactones produced in the culture, again facilitating the production of mycolactones in commercially relevant quantities.

In a third embodiment, the present invention also provides a robust and scalable method for the purification of mycolactones based on extraction and chromatography. Prior to the present invention, mycolactone was purified by TLC. While one can obtain sufficient amounts of mycolactone using TLC-based purification to determine its structure and conduct limited in vitro and ex vivo testing, such methods are not practical for the production of mycolactones in amounts required for pre-clinical in vivo testing and for clinical trials.

In a fourth embodiment the present invention provides novel mycolactone compounds isolatable from *Mycobacterium ulcerans* in purified form. The improved fermentation methods and media formulations as well as the improved purification methods of the invention have enabled the detection, isolation, and purification of novel mycolactone compounds produced in *M. ulcerans* that have previously not been detected. Two such novel compounds are described below. Both are produced at lower levels than mycolactones A and B, and one of the novel compounds, designated mycolactone C, is produced at a significantly higher level than the other, designated mycolactone D.

Mycolactone C has a molecular mass 16 daltons lower than mycolactone A and B, indicating the loss of an oxygen atom relative to the known compounds. Initial characterization of mycolactone C indicates that the absent oxygen atom is from the fatty acid like portion of mycolactone A and B. Initial characterization of mycolactone D indicates that these compounds are dehydration products of mycolactones A and B.

Thus the novel methods of the invention for the production and purification of the mycolactones have enabled not only the production of mycolactones A and B in quantities suitable for testing but also the identification of previously unidentified mycolactones C and D.

The compounds of the invention can be readily formulated to provide the pharmaceutical compositions of the invention. The pharmaceutical compositions of the invention can be used in the form of a pharmaceutical preparation, for example, in solid, semisolid, or liquid form. This preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use.

The carriers which can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used. For example, the compounds of the invention may be utilized with hydroxypropyl methylcellulose essentially as described in U.S. Pat. No. 4,916,138, incorporated herein by reference, or with a surfactant essentially as described in EPO patent publication No. 428,169, incorporated herein by reference.

Oral dosage forms may be prepared essentially as described by Hondo et al., 1987, *Transplantation Proceedings XIX*, Supp. 6: 17–22, incorporated herein by reference. Dosage forms for external application may be prepared essentially as described in EP Pub. No. 423,714, incorporated herein by reference. The active compound is included in the pharmaceutical composition in an amount sufficient to produce the desired effect upon the disease process or condition.

For the treatment of conditions and diseases caused by infection, immune system disorder (or to suppress immune function), or cancer, a compound of the invention may be administered orally, topically, parenterally, by inhalation spray, or rectally in dosage unit formulations containing conventional non-toxic pharmaceutically acceptable carriers, adjuvant, and vehicles. The term parenteral, as used herein, includes subcutaneous injections, and intravenous, intrathecal, intramuscular, and intrasternal injection or infusion techniques.

Dosage levels of the compounds of the present invention are of the order from about 0.01 mg to about 100 mg per kilogram of body weight per day, preferably from about 0.1 mg to about 50 mg per kilogram of body weight per day. The dosage levels are useful in the treatment of the above-indicated conditions (from about 0.7 mg to about 3.5 mg per patient per day, assuming a 70 kg patient). In addition, the compounds of the present invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain from 0.5 mg to 5 $\mu$m of active agent compounded with an appropriate and convenient amount of carrier material, which may vary from about 5 percent to about 95 percent of the total composition. Dosage unit forms will generally contain from about 0.5 mg to about 500 mg of active ingredient. For external administration, the compounds of the invention may be formulated within the range of, for example, 0.00001% to 60% by weight, preferably from 0.001% to 10% by weight, and most preferably from about 0.005% to 0.8% by weight.

It will be understood, however, that the specific dose level for any particular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

In another embodiment, the present invention provides a method of treating cancer, which method comprises administering a therapeutically effective amount of a novel epothilone compound of the invention.

The following examples are given for the purpose of illustrating the present invention and shall not be construed as being a limitation on the scope of the invention or claims.

EXAMPLE 1

Production of Mycolactones by Fermentation

A. Production in Plates

A primary plate is prepared as follows. A 2 mL culture of *Mycobacterium ulcerans* (161 SWT, from NIH, but any mycolactone producing Mycobacterium species can be employed in accordance with the methods of the invention) is spread evenly on a 150×15 mm M7H9 agar plate using a sterile spreader. The plate is incubated at 30° C. for 4–8 weeks or when significant growth (yellow, waxy colonies) appears on the plate. Secondary plates can be made by streaking colonies from the primary plate or from liquid culture.

B. Production in T-Flasks

A primary T-flask is prepared as follows. About 10 mL of M7H9 liquid medium is poured onto the surface of a plate (see above) containing *Mycobacterium ulcerans* colonies. A sterile spreader is used to loosen the colonies from the agar, and a sterile serological pipette is then used to transfer the loose colonies onto a 600 mL T-triple flask containing 300 ml of M7H9 medium. The T-flask is then incubated at 30° C. for 4–8 weeks or until significant growth (yellow, clumpy cells) is observed. In a typical experiment, the amount of mycolactones recovered from 1.8L of broth using M7H9 medium was 3 mg, and the approximate titer was 3 mg/1.8 L or 1.7 mg/L.

Secondary or successive T-flasks can be made using culture from the primary T-flask or other T-flasks by the addition of 100 mL of culture to 200 mL of M7H9 medium.

C. Production in Spinner Flasks

M7H9 medium is added to a spinner flask at a desired volume and inoculated with liquid culture from T-flasks at a 10% inoculum volume. The spinner flask is placed in a 30° C. warm room on a magnetic stirring plate and stirred at a speed that will result in adequate mixing to keep cellular clumps in suspension. The spinner flask is incubated for 4–8 weeks or until mycolactone concentration detected in the broth reaches a plateau.

A variety of experimental parameters have been tested, including: 80–100 mL total volume in a 100 mL spinner flask (Bellco) agitated at 300–400 rpm; 175–210 mL total volume in a 250 mL spinner flask (Bellco) agitated at 200–300 rpm; 300–350 mL total volume in a 500 mL spinner flask (Bellco) agitated at 150–250 rpm; 6.7 L total volume in a 15 L spinner flask (Bellco) agitated at 100–150 rpm; and 10 L total volume in a 15 L spinner flask (Coming) agitated at 50–100 rpm. The amount of mycolactones recovered from 6 L of broth from a 15L spinner flask using M7H9 medium with 2% egg yolk enrichment was 28 mg, yielding an approximate titer of 28 mg/6 L or 4.7 mg/L. Optical density (O.D.) was used to monitor cell density and growth of the bacterial culture using a spectrophotometer at a wavelength of 600 nm.

D. Production in Fermentor

M7H9 medium is added to a fermentor at a desired volume and inoculated with liquid culture from T-flasks or spinner flasks at a 10% inoculum volume. The culture is maintained at the following parameters for the duration of the run: pH=6.5+/−0.1, temperature=30+/−0.1° C., dissolved oxygen=50% +/−20%, airflow=<1 LPM, agitation= 500+/−200 rpm. The pH is controlled via addition of acid (2.5N $H_2SO_4$) and base (2.5N NaOH). The duration of the fermentor run is for 4–8 weeks or until mycolactone concentration detected in the broth reaches a plateau. The amount of mycolactones recovered from 8.5 L of broth from a 10 L fermentor (B. Braun Biostat B) was 30 mg, yielding an approximate titer of 3.5 mg/L. Dry cell weight (DCW) was used to monitor the cell density and growth of the bacterial culture.

The DCW procedure is as follows.

1) Place 40 mL of well-mixed broth in a 50 mL conical falcon tube (tared).
2) Spin down at 3300 g in a centrifuge for 10 minutes.
3) Decant supernatant.
4) Add 40 mL of water to pellet and resuspend by shaking or vortexing.
5) Spin down again at 3300 g in a centrifuge for another 10 minutes.
6) Place tube in an 80° C. oven for >24 hours and re-weigh.
7) Calculate DCW by: [(Dried Pellet+Tube)−(Tare of Tube)]/40 mL In one fermentor experiment, the maximum DCW achieved was 1.4 g/L.

EXAMPLE 2

Mycolactone LC/MS Analysis

For analysis of mycolactone by LC/MS, add 1 mL of methanol to 1 mL of broth in a 1.5 mL eppendorf tube. Spin the sample using a microcentrifuge set at 13,000 rpm for 5 minutes. Remove the MeOH extract, and filter it through a 0.45 gm syringe filter if necessary (if extract is cloudy and contains particulates), and place the extract into a sample vial for LC/MS analysis.

EXAMPLE 3

Harvest of *Mycobacterium ulcerans* Culture

To harvest the culture, measure the volume of culture broth and to it add an equal volume of MeOH. Let the solution mix for 20–30 min. Separate the solids from the extract by either pouring broth into centrifuge bottles and centrifuging for 30 min. at 10,800 g or by using a depth filter. The extract is then ready for purification.

EXAMPLE 4

| Medium Preparation M7H9 Medium | |
|---|---|
| Component | Concentration (g/L) |
| Ammonium Sulfate | 0.5 |
| Monopotassium Phosphate | 1.0 |
| Disodium Phosphate | 2.5 |

-continued

Medium Preparation
M7H9 Medium

| Component | Concentration (g/L) |
| --- | --- |
| Sodium Citrate | 0.1 |
| Magnesium Sulfate | 0.05 |
| Calcium Chloride | 0.0005 |
| Zinc Sulfate | 0.001 |
| Copper Sulfate | 0.001 |
| L-Glutamic Acid | 0.5 |
| Ferric Ammonium Citrate | 0.04 |
| Pyridoxine | 0.001 |
| Biotin | 0.0005 |
| Glycerol | 2 ml/L |

To prepare the M7H9 medium, combine the M7H9 medium components in 900 mL of water, sterilize by autoclaving at 121° C. for 30 min., cool to room temperature, and add 100 mL of OADC enrichment. M7H9 medium can be obtained in a pre-formulated powder form (Difco) to which 4.7 g of the powder is added to 900 mL of water with the addition of 2 mL of glycerol. The medium is sterilized as described, and 100 mL of OADC enrichment is added. Autoclave time increases as the volume of the medium increases (i.e., autoclave time for 10 L medium in a spinner flask is 120 min.).

| OADC Enrichment | |
| --- | --- |
| Component | Concentration (g/L) |
| Oleic Acid | 0.5 |
| Albumin Fraction V, Bovine | 50.0 |
| Dextrose | 20.0 |
| Catalase (Beef) | 0.04 |
| Sodium Chloride | 8.5 |

To prepare OADC enrichment, combine the above components in water and bring the volume to 1 L. Sterilize the mixture with a sterile filter housing with a 0.2 μm nylon membrane. OADC enrichment can also be obtained in pre-formulated liquid form (BBL).

For M7H9 agar (used in plates), 15 g/L of Bacto agar is added to M7H9 before autoclaving. The medium is then autoclaved as described above and allowed to cool to 50–55° C., at which time 100 mL of OADC are added. The medium is poured onto 150×15 mm plates before it solidifies.

The present invention also provides new media formulations that increase growth rate and production of the mycolactones. One such improved formulation is prepared by doubling the concentration of M7H9 components, including OADC enrichment. Another formulation involves the addition of 50% egg yolk enrichment (Difco), which comes in liquid form, to M7H9 medium as a post-sterile addition at a concentration of 20 ml/L or 2%.

EXAMPLE 5

Purification of Mycolactones

Mycolactones A and B were isolated as an isomeric mixture (28 mg) from 6 L of *Mycobacterium ulcerans* culture broth. Two new compounds, also as isomeric mixtures, were also isolated. HPLC (diode array) and LC/MS data indicate that the more abundant of the two new compounds, designated mycolactone C, is a desoxymycolactone, while the minor component is a mycolactone dehydration product.

Whole broth (6 L) was mixed with an equal amount 100% methanol (Fisher bulk). The mixture was centrifuged (1500× g, 5 minutes) and the centrate loaded onto a HP20 (Mitsubishi with SPE resin) capture column (4.8×25 cm). The column was eluted with 3 L of 100% methanol, which was evaporated to dryness. The resulting solids were extracted twice with 100 mL of 100% methanol. Following filtration the filtrates were combined and evaporated, giving 1.16 g of a dark oil. The oil was dissolved in 20 mL of 100% methanol to which 20 mL of deionized water were added. The resulting suspension was chromatographed on a 1×25 cm C18 (Bakerbond, 40 μm C18 resin) chromatography column previously equilibrated with 50% methanol in water. Column elution was carried out in a step gradient fashion starting with 80%, then 90%, and finally 100% methanol. Five fractions were collected. Fraction changes were made with the aid of on-line UV monitoring at 360 nm. Fractions were evaporated and re-dissolved in 10 mL of acetone, filtered and dried.

Figure 1:
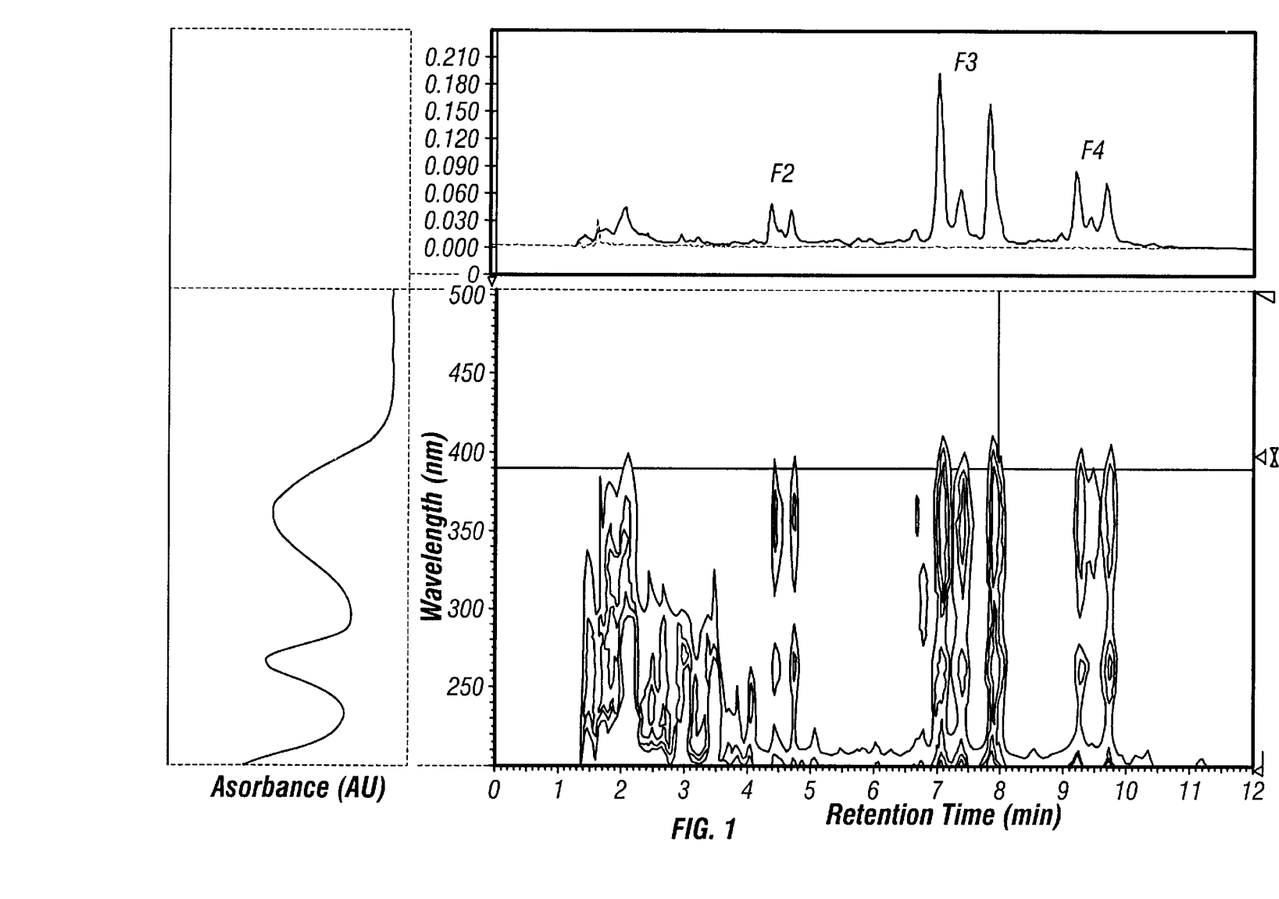
FIG. 1 shows an HPLC chromatogram (top) and diode array spectra (bottom) of the solid phase extraction product of mycolactones prepared and purified in accordance with the methods of the invention. The HPLC chromatogram shows three distinct peak regions labelled F2 (fraction 2), F3 (fraction 3), and F4 (fraction 4). There are similar peak profiles within each region with respect to relative peak intensities, retention times, and diode array spectra. Fraction 3 contains mycolactones A and B. Fraction 2 contains a mixture of dehydrated mycolactones, termed mycolactone D. Fraction 4 contains a group of isomers with one less oxygen than mycolactones A and B, termed mycolactone C.

HPLC data of the solid phase extraction product showed three distinct peak regions (see FIG. 1). Examination revealed similar peak profiles within each region with respect to relative peak intensities, retention times, and diode array spectra. C18 column chromatography was used to separate the three regions into three fractions. Fraction 3 (28 mg) contained mycolactones A and B. Mass spectra data on fraction 2 indicated a mixture of dehydrated mycolactones, while data for fraction 4 indicated a group of isomers with one less oxygen than mycolactones A and B.

The structure of mycolactone B is shown below.

Mycolactone B
$C_{44}H_{70}O_9$
Calculated Exact Mass: 742.50
Mol. Wt.: 743.02

In another example, mycolactones A and B were isolated as an isomeric mixture (32 mg) from 10.3 L of *Mycobacterium ulcerans* broth. HPLC (UV 360 nm) data showed a complex mixture of peaks corresponding to mycolactones A and B as well as other minor isomers. Compound identification was made on the basis of HPLC (diode array), LC/MS, and NMR data obtained on a mycolactone A and B mixture. Individual mycolactones were isolated as enriched isomeric fractions using semi-preparative HPLC. When samples were shielded from laboratory light, the individual mycolactones were stable. Samples exposed to laboratory lighting showed substantial isomerization after 52 hours.

Whole broth (1.8 L) was mixed with an equal amount 100% methanol (Fisher ACS grade). The mixture was allowed to settle for 30 minutes. The mixture was decanted and the resulting solution loaded onto a solid phase extraction column (4.8×25 cm) containing HP20 (Mitsubishi HP20 SPE resin) previously equilibrated with 50% methanol in water. Loading of the extract was carried out at 100 mL/minute. The column was eluted with 3 L of 100% methanol in water. The first 250 mL were discarded while the remainder of the eluant was collected as a single fraction. The solid phase extraction product pool (2.5 L) was evaporated to dryness using a Buchi R153 (20 L, 40° C.) rotary evaporator ("rotovap"). This gave a red glass, which was extracted with 100 mL of 100% methanol in water, filtered through Whatman #4 filter paper, and evaporated to dryness (vacuum oven, 10 mbar, 40° C.). The dry material (280 mg) was dissolved in 50 mL of 100% methanol to which 50 mL of water were added. The suspension was loaded onto a 1×25 cm C18 (Bakerbond C18 resin, 40 μg) chromatography column previously equilibrated with 50% methanol in water. Loading and elution flow rate was 4 mL/minute. The column was eluted with 120 mL of 80% methanol in water followed by 120 mL of 90% methanol in water. A total of 24×10 mL fractions were collected with fractions 12–16 being combined and taken as the best pool. Evaporation gave 11 mg of a yellow oil. This material was triturated with 2 mL of acetone, filtered through a 0.25 um filter, and evaporated to give 3 mg of a yellow oil.

In another example, whole broth (8.5 L) was mixed with an equal amount of 100% methanol. The mixture was centrifuged (30 minutes at 10,800×g), decanted, and the resulting extract loaded onto a solid phase extraction column (4.8×25 cm) containing HP20 previously equilibrated with 50% methanol in water. Loading of the extract was carried out at 100 mL/minute. The column was eluted as one fraction with 5 L of 100% methanol. The methanol eluant was evaporated to dryness using a 20 L Buchi rotovap, and the resulting solids were extracted with 100 mL of 100% methanol, vacuum filtered through Whatman #4 filter paper, and evaporated using a R124 Buchi rotovap (2 L, 40° C.). The oil was dissolved in 50 mL of 100% methanol and diluted with 50 mL of water to form a suspension, which was loaded onto a pre-equilibrated 1×25 cm C18 chromatography column. The column was eluted with 240 mL (12 column volumes) of 85% methanol. A total of 24×10 mL fractions were collected and assayed by HPLC. Fractions 10–16 were combined and evaporated using a R124 Buchi rotovap to give 42 mg of a yellow oil. The oil was triturated with dichloromethane, filtered through glass wool and dried to give 36 mg of a yellow oily material. This material was triturated with 10 ml of acetone, filtered through a small plug of glass wool, and evaporated using a R124 Buchi rotovap. This gave 30 mg of a yellow oil. Mycolactone mixtures, each containing mycolactone A and B, were combined to give a 33 mg of a yellow oil.

The individual components of the mycolactone mixture were separated using semi-preparative HPLC. The column used was an Inertsil ODS3 5 μm (1×25 cm) semi-preparative HPLC column. A gradient HPLC method starting with 65:35 acetonitrile in water and ending with 100% acetonitrile was used over a run time of 16 minutes. Four 100 μL injections were used. 16 mg of material were used as starting material. For each run, three fractions were collected. Fraction changes were based on on-line monitoring at 400 nm.

In another example, an enriched fraction (33 mg) containing mycolactone A and B isomers was isolated from a total of 10.3 L of whole broth. HPLC diode array data of the enriched fraction showed a complex mixture of peaks all containing a primary UV maximum at 360 nm and a second maximum at 260 nm. The strong absorbance at 360 nm was diagnostic for the mycolactones and allowed for tracking of the various isomers. HPLC (diode array), along with LC/MS and NMR data confirmed the presence of mycolactones A and B in this mixture. Semi-preparative HPLC was carried out on 16 mg of the isomeric mixture and yielded 2 substantially enriched isomeric fractions. The enriched samples were shielded from laboratory light. Evaporation of pools B and D gave 2 and 4 mg of yellow oils.

To monitor stability of the individual enriched isomers, HPLC data was collected on samples stored in the presence and absence of laboratory light. Measurements were made on samples stored in methanol at 23° C. Initial HPLC sampling was carried out on individual isomers shielded to minimize exposure to laboratory light. These same samples were allowed to remain in the autosampler, shielded from light, for 72 hours before additional HPLC data was collected. Following this, the samples were stored on a lab bench exposed to laboratory light for 52 hours, at which time the final HPLC data time point was collected. Under these conditions, samples that were shielded from light remained stable, showing no change in their respective HPLC chromatograms. However samples exposed to light for 52 hours showed substantial isomerization.

EXAMPLE 6

Production of Mycolactones

Like other pathogenic Mycobacteria, *M. ulcerans* grows slowly, with a doubling time of 1–2 days, and the cells form aggregates in liquid media. Cultivation of *M. ulcerans* for 4–6 weeks in stationary T-flasks containing M7H9/OADC medium yields a final dry cell weight of ca. 1.4 g/L and mycolactone titers of 4–6 mg/L (George, K. M., et al., *Sci.* (1999) 283:854–857), a cumbersome process for producing the compound. Here we describe the adaptation of *M. ulcerans* to suspension culture in spinner flasks and development of a scalable process for producing mycolactones in larger quantities. A fed-batch fermentation process was implemented up to the 150 L scale and several new mycolactone congeners were identified.

Materials and Methods

Strain and Media. *Mycobacterium ulcerans*, strain 1615 (Trudeau Collection Strain, Lake Saranac, N.Y.) was obtained from Dr. Pam Small. The culture was initially grown on M7H9/OADC agar plates at 30° C. for 4–8 weeks (until yellow colonies were well formed). Cultures in M7H9/OADC medium were brought to 15% glycerol and samples were stored at −80° C. to provide a consistent source of inocula.

Difco M7H9 powder (4.7 g) was dissolved in 900 mL deionized water containing 2 mL/L glycerol and sterilized by autoclaving at 121° C. for 30 min. After autoclaving, the medium was cooled to room temperature before OADC enrichment (oleic acid, albumin, dextrose, and catalase, pre-formulated from Difco) was added to a concentration of 100 mL/L of medium. To prepare plates, 15 g/L agar was added to the M7H9 basal medium before autoclaving and plates were poured immediately after adding OADC enrichment to the medium at 50° C. In some experiments liquid egg yolk enrichment (Difco) was added to a final concentration of 20 mL/L (Palomino, J. C., et al., {*J Clin. Microbiol.* (1998) 36:402–408).

T-Flask cultivation. To a plate containing *M ulcerans* colonies M7H9/OADC medium (10 mL) was added and a sterile spreader was used to detach the cells. The suspended cells were transferred into a 600 ml T-flask (triple layer, Nunc) containing 300 mL of M7H9/OADC medium and the flask was incubated at 30° C. for 4–8 weeks (until significant growth was observed). Cultures were expanded by adding 100 mL of culture to 200 mL of fresh M7H9/OADC medium.

Growth in spinner flasks. A spinner flask containing the desired volume of M7H9/OADC medium was inoculated with a 10% volume of liquid culture and incubated at 30° C. for 4–8 weeks, or until mycolactone production ceased. Conditions depended on the spinner flask used (Bellco 100 ml spinner: 80–100 ml working volume, 300–400 rpm; Bellco 250 ml spinner: 175–210 ml working volume, 200–300 rpm; Bellco 500 ml spinner: 300–350 ml working volume, 150–250 rpm; Bellco 15 L spinner: 6.7 L working volume 100–150 rpm; Corning 15 L spinner: 10 L working volume, 50–100 rpm).

Growth in stirred-tank fermenters. M7H9/OADC medium, with or without 2% egg yolk, was used in fermentation studies. The following parameters were maintained: pH 6.5∓0.1; 30° C.±0.1° C.; 50%±20% dissolved oxygen; airflow $\leq$1 LPM; 500±200 rpm agitation. The pH was controlled by adding 2.5N $H_2SO_4$ or 2.5N NaOH. Fermentation continued for 4–8 weeks until mycolactone production had ceased. The glucose concentration in culture samples was measured using a YSI glucose analyzer.

Analysis of mycolactones. Whole culture broth samples were prepared for analysis by adding an equal volume of methanol and removing insoluble material by centrifuging at 12,000 g. Mycolactones were resolved and quantitated using a Hewlett Packard 1090HPLC with UV detection at 360 nm. Supernatant (250 $\mu$l) was injected and the mycolactones captured on a 4.6×10 mm column (Inertsil, C18 ODS-3, 5 $\mu$m). After washing with 50% acetonitrile for 2 minutes the mycolactones were eluted and resolved on a 4.6×150 mm column (Inertsil, C18 ODS-3, 5 $\mu$m) with a 24 minute gradient from 50% to 100% acetonitrile. In some cases, mycolactones were analyzed using a system comprised of a Beckman System Gold HPLC, an Alltech ELSD detector, and a PE SCIEX API100LC MS-based detector equipped with an atmospheric pressure chemical ionization source. Fractions of interest were analyzed on a Applied Biosystems Mariner time-of-flight mass spectrometer with a turbo ion-spray source.

Other microbiological methods. Dry cell weight was determined by centrifuging a 40 mL sample of culture for 10 minutes at 3300 g in a pre-weighed 50 mL centrifuge tube, decanting the supernatant, washing the cell pellet with 40 mL water, drying in an 80° C. oven, and weighing the pellet. Acid fast staining was done with the Acid-Fast BactiStain kit from Polysciences according the manufacturer's instructions.

Results and Discussion

Adaptation of the Cells to Growth in Suspension

Figure 2:
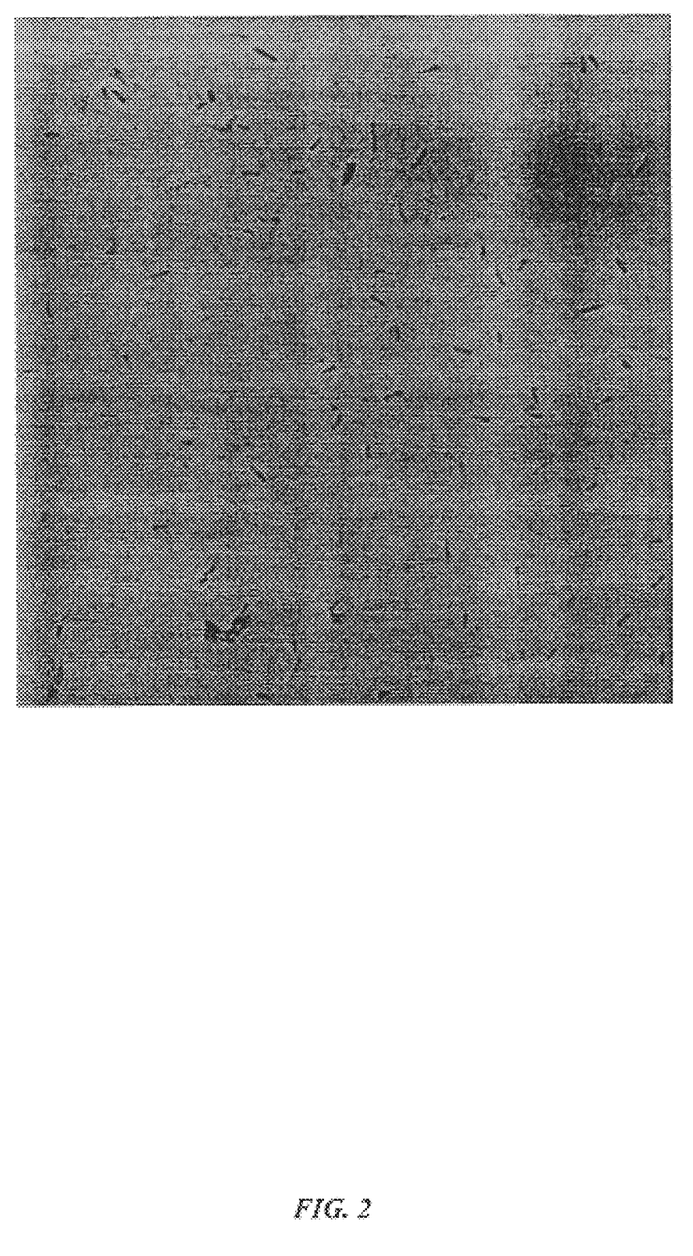
FIG. 2 depicts an acid fast staining of a spinner flask culture.

For a scalable process, it was necessary to adapt the cells to growth in suspension. T-flask cultures were used to inoculate M7H9/OADC medium in a variety of vessel configurations, including baffled flasks, flasks fitted with stainless steel springs, and spinner flasks designed for growth of suspension-adapted animal cells. Because more dispersed growth of *M. ulcerans* has been reported with addition of Tween 80 (Mve-Obiang, A., et al., *FEMS Microbiol. Lett.* (1999) 181:153–157; Power, D. A., et al., *Am. Rev. Resp. Dis.* (1965) 92:83–93), this was also investigated. All the shake flask conditions tested, with or without Tween 80, gave severe aggregation of the cells, poor growth, and negligible mycolactone production. Surprisingly, however, spinner flask cultures gave dispersed growth. Acid-fast staining and microscopic examination (FIG. 2) shows that the cultures were mostly individual rods with a few clumps consisting of only a few cells. Such dispersed growth has not been reported previously for any slow growing mycobacterial species.

Figure 3A:
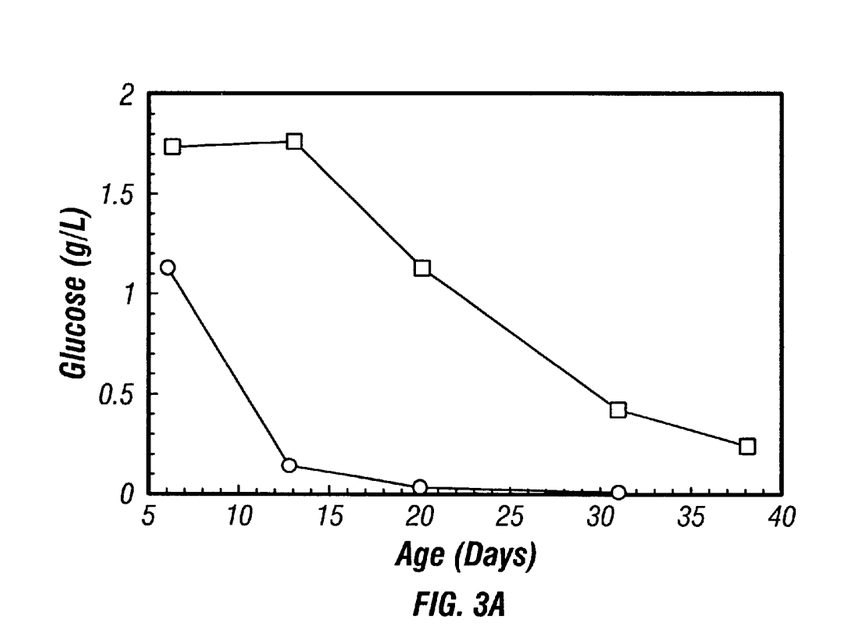
FIGS. 3a–b are comparisons of strains adapted and not adapted to suspension culture. Spinner flasks (100 mL) were inoculated with a culture from a spinner flask (●) or stationary T-flask (■). (A) Glucose concentration (g/L) and (B) mycolactone titers (mg/L) are plotted as a function of time post inoculation.
Figure 3B:
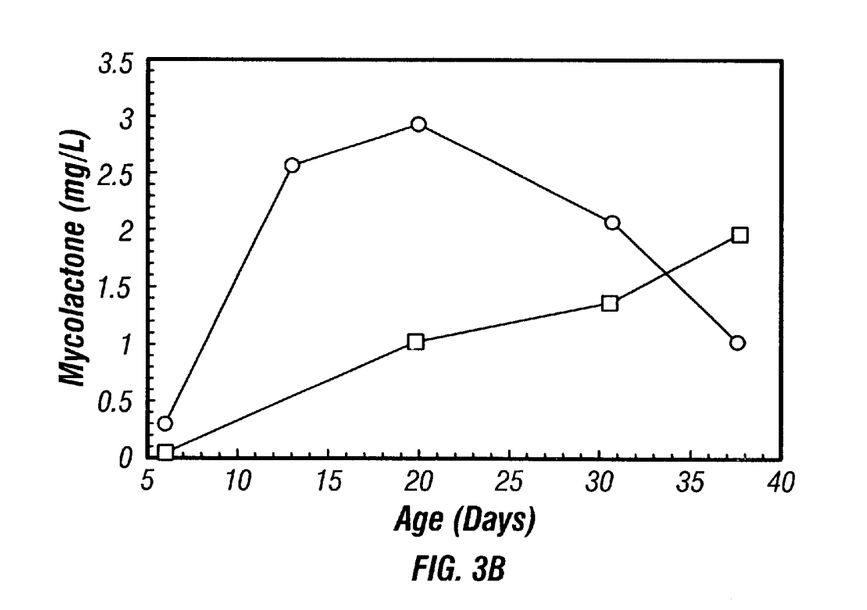

To demonstrate that the cells had been adapted to dispersed growth, identical spinner flasks were inoculated with a 10% volume of culture from a T-flask and from a spinner flask. By comparing the rates of glucose consumption and mycolactone production in these cultures (FIG. 3), it is clear that significant adaptation occurred during growth in the spinner flask.

Cell density was difficult to measure and an accurate growth rate could not be obtained from the spinner flask cultures. Also, degradation of mycolactones was often observed at later time points, indicating the importance of monitoring production closely to permit harvest at the maximum titer. Although low oxygen tension has been reported to enhance *M. ulcerans* growth (Palomino, J. C., et al., *J. Clin. Microbiol.* (1998) 36:3420–3422), we did not observe any obvious enhancement in growth by reducing air flow.

Detection of Additional Mycolactones

Figure 4A:
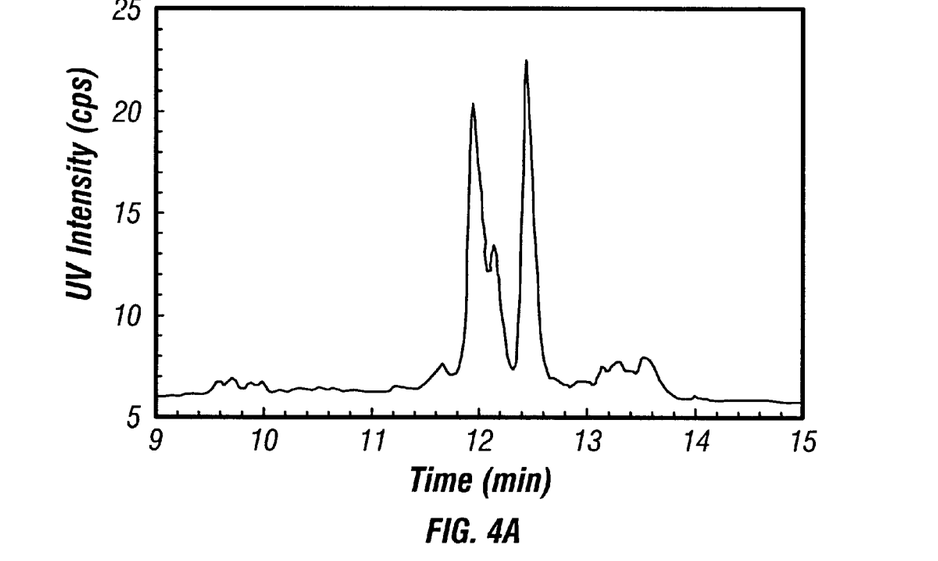
FIGS. 4a–b are observations of new mycolactone congeners. Spinner flask cultures in (FIG. 4a) M7H9/OADC or (FIG. 4b) M7H9/OADC containing 2% egg yolk were analyzed 20 days after inoculation by LC-MS. Shown are the elution profiles at 360 nm. The indicated regions were purified and concentrated for mass spectral analysis and the predominant mass is given.
Figure 4B:
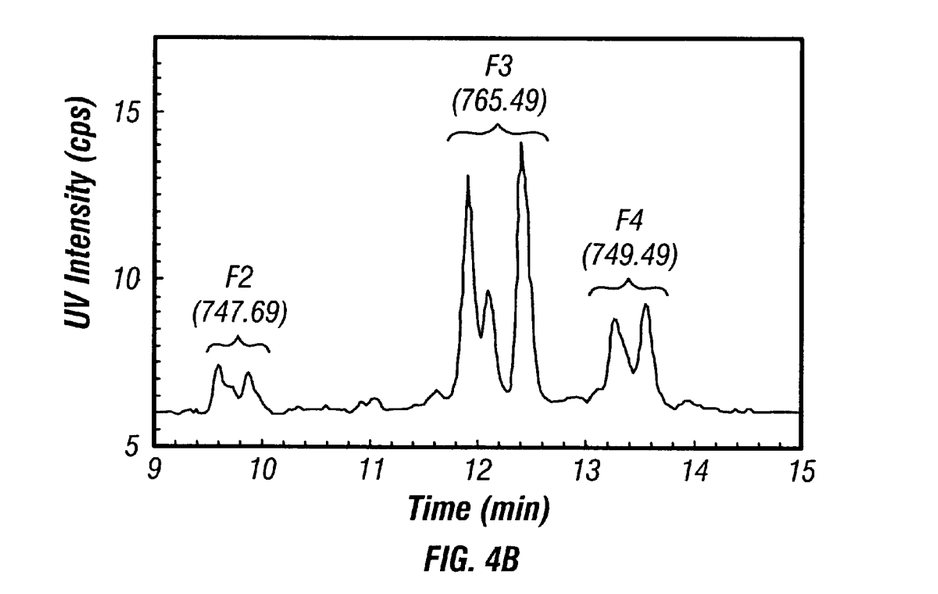

Mycolactones A and B are double bond isomers with the same mass (Gunawardana, G., et al., *J. Am. Chem. Soc.* (1999) 121:6092–6093). Under our reverse-phase HPLC conditions, these isomers are resolved and elute in the 12.0–12.5 minute region (FIG. 4a). The order that A and B elute has not been established and another peak was observed between A and B which represents yet another mycolactone isomer by LC/MS analysis. Although the structure of this new isomer has not been determined, we presume it represents isomerization at a different double bond. Addition of egg yolk to mycobacterial media has been reported to be beneficial (Palomino, J. C., et al., *J. Clin. Microbiol.* (1998) 36:402–408) and we found this addition generally increased mycolactone titers. Moreover, new compounds with the same UV spectrum as mycolactones A and B were readily observed which eluted from the column at significantly different retention times (FIG. 4b). Material that eluted in the regions around 9.7 and 13.5 minutes was separately collected and analyzed by mass spectrometry. The material eluting around 13.5 minutes gave a prominent [M+Na]+at m/z 749.5 and a weak pseudo-molecular ion at m/z 727.5, corresponding to a mycolactone congener with one less oxygen atom. The material eluting around 9.7 minutes gave a prominent ion at m/z 747.5, which presuming it is also a sodium adduct, would correspond to mycolactones A and B with one less oxygen atom and two less hydrogen atoms. Although these new mycolactone congeners could be detected when the strain was cultivated in the absence of egg yolk, its addition greatly facilitated the analysis. The masses of these new mycolactone congeners are consistent with compounds that could arise by different β-keto processing on a putative type I PKS. The difference of an oxygen atom could, alternatively, be due to a difference in the extent of a putative hydroxylase reaction. The ratio of areas for each group of peaks eluting at the three regions are very similar (FIG. 4b), suggesting that the same equilibrium mixture of double bond isomers is reached for each congener. Equilibration between mycolactones A and B was found to occur only when the sample was exposed to ambient light (data not shown), which is consistent with double bond isomerization.

Scale-Up to Stirred-Tank Fermenters

Figure 5A:
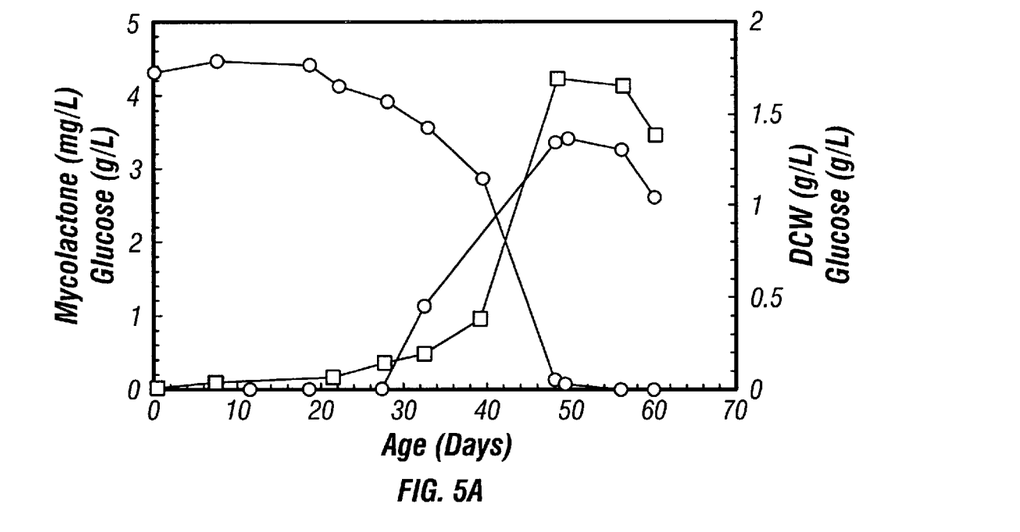
FIG. 5 depicts mycolactone production in stirred-tank fermenters. Shown are data for a 10 L working volume of M7H9/OADC (A) and a 150 L working volume of M7H9/OADC plus 2% egg yolk (B). Glucose concentration (g/L) (■) and mycolactone titer (mg/L) (●) are shown as a function of days post-inoculation for both fermentations. Dry cell weight (g/L) (O) is shown only for the 10 L fermentation; egg yolk interfered with this measurement in the 150 L fermentation.

Based on success with the spinner flasks, fermentations were also carried out in stirred tank fermenters. FIG. 5a shows a fermentation in a 10 L fermenter using a 400 mL inoculum (4%) from a spinner flask culture. In this fermentation there was a long lag period before glucose utilization and mycolactone production began. However, additional work in spinner flasks showed that larger inoculum volumes greatly reduced this lag period. Mycolactone production ceased at approximately the same time that glucose was depleted from the medium, suggesting that adding more glucose could be beneficial.

Figure 5B:
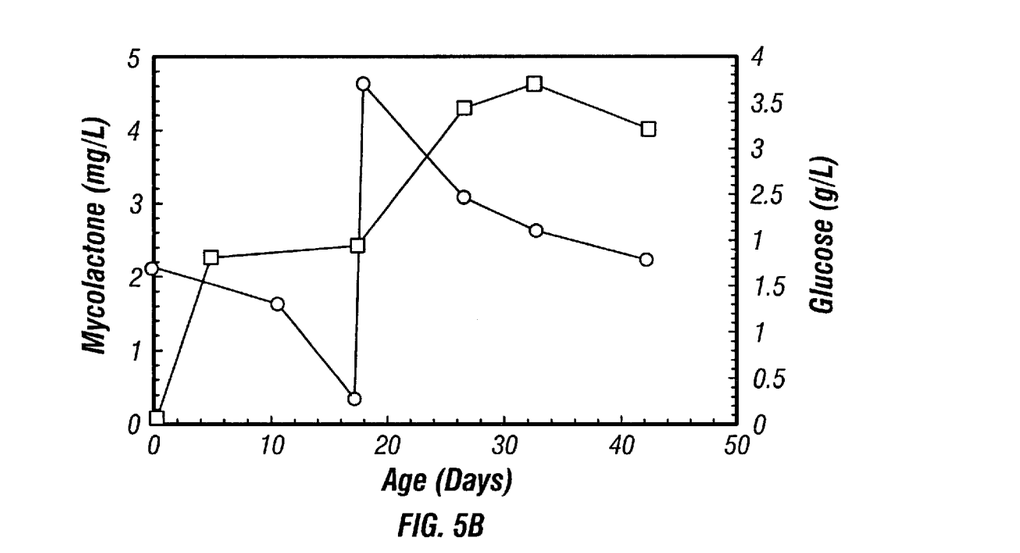

Using data from the 10 L fermentation and several spinner flask experiments, *M. ulcerans* cultivation was scaled up to a 150 L fermenter using M7H9/OADC supplemented with 1% egg yolk (FIG. 5*b*). A 10% inoculum was used to reduce the lag phase. The glucose concentration decreased to <0.5 g/L on day 17, at which point additional glucose was added to prevent carbon limitation. Glucose continued to be consumed at a rapid rate until about day 26. The additional glucose may have caused the increase in mycolactone production. Since more than 2 g/L of glucose remained in the culture when growth had ceased, another essential nutrient may become limiting. Although we have developed a scalable process, mycolactone titers were essentially the same as observed in T-flasks. However, this process is amenable to further development that should lead to increased titers.

Recovery of Mycolactones from the Culture

The distribution of mycolactones between the solid and soluble fractions of culture broth was analyzed in samples from M7H9/OADC with or without added egg yolk. The distribution between pellet and supernatant fractions was approximately equal with M7H9/OADC alone, but addition of egg yolk shifted the distribution such that over 95% of the mycolactones were in the pellet fraction. These data suggest that mycolactones are secreted from the cells, but remain associated with suspended lipids. Thus, in addition to enhancing titer, supplementation with egg yolk can simplify downstream processing.

The invention having now been described by way of written description and examples, those of skill in the art will recognize that the invention can be practiced in a variety of embodiments and that the foregoing description and examples are for purposes of illustration and not limitation of the following claims.

What is claimed is:

1. A method for the production of mycolactones, which method comprises the steps of cultivating *Mycobacterium ulcerans* cells in a dispersed suspension culture by fermentation in stirred tanks or in spinner flasks, wherein said cells are cultivated in OADC enriched medium, extracting said medium with methanol to produce a crude extract, and purifying the mycolactones from the crude extract by liquid chromatography.

2. A method for the production of mycolactones, which method comprises the steps of cultivating *Mycobacterium ulcerans* cells in a dispersed suspension culture by fermentation in stirred tanks, wherein said cells are cultivated in OADC enriched medium, extracting said medium with methanol to produce a crude extract, and purifying the mycolactones from the crude extract by liquid chromatography.

3. A method for the production of mycolactones, which method comprises the steps of cultivating *Mycobacterium ulcerans* cells in a dispersed suspension culture in spinner flasks, wherein said cells are cultivated in OADC enriched medium, extracting said medium with methanol to produce a crude extract, and purifying the mycolactones from the crude extract by liquid chromatography.

4. The method claim 1, 2, or 3, wherein the OADC-enriched medium is further enriched by the addition of egg yolk.

5. The method of claim 1, 2, or 3, wherein said enriched medium is medium at a 1× concentration.

6. The method of claim 1, 2, or 3, wherein said 1× concentration is doubled.

* * * * *